US011576558B2

(12) United States Patent
Scutti et al.

(10) Patent No.: US 11,576,558 B2
(45) Date of Patent: Feb. 14, 2023

(54) MEDICAL VALVE

(71) Applicant: Boston Scientific Scimed, Inc., Maple Grove, MN (US)

(72) Inventors: James J. Scutti, Norwell, MA (US); Robb Morse Gavalis, Westborough, MA (US); Allyn Narcisse Jensrud, Brookline, MA (US); Larry Edward Stanton, Burlington, MA (US); Colby Harris, Weston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 253 days.

(21) Appl. No.: 16/887,206

(22) Filed: May 29, 2020

(65) Prior Publication Data
US 2020/0375434 A1 Dec. 3, 2020

Related U.S. Application Data

(60) Provisional application No. 62/854,689, filed on May 30, 2019.

(51) Int. Cl.
*A61B 1/00* (2006.01)
*A61B 1/015* (2006.01)
(52) U.S. Cl.
CPC ...... *A61B 1/00068* (2013.01); *A61B 1/00137* (2013.01); *A61B 1/015* (2013.01)
(58) Field of Classification Search
CPC ....... A61M 2039/2493; A61B 1/00068; A61B 1/00137; A61B 1/015; F16K 11/0716
USPC .......................................... 604/167.01–0.06
See application file for complete search history.

(56) References Cited

U.S. PATENT DOCUMENTS

| 2010/0024818 A1* | 2/2010 | Stenzler | A61M 16/208 604/533 |
| 2016/0199548 A1* | 7/2016 | Cheng | A61M 1/0062 604/30 |
| 2019/0125167 A1* | 5/2019 | Taniguchi | A61B 1/0661 |

FOREIGN PATENT DOCUMENTS

| JP | S5810030 A | 1/1983 | |
| JP | S59140702 U | 9/1984 | |
| WO | 2012/075131 A1 | 6/2012 | |
| WO | 2015/080694 A1 | 6/2015 | |
| WO | 2018/136274 A1 | 7/2018 | |
| WO | WO-2018142831 A1 * | 8/2018 | ......... A61B 1/00068 |
| WO | 2019/040888 A1 | 2/2019 | |

(Continued)

OTHER PUBLICATIONS

WO-2018142831-A1 Espacenet English Translation (Year: 2018).*
WO-2020039595-A1 Espacenet English Translation (Year: 2018).*

*Primary Examiner* — Michael J Carey
*Assistant Examiner* — Megan Elizabeth Monahan
(74) *Attorney, Agent, or Firm* — Bookoff McAndrews, PLLC

(57) ABSTRACT

A valve for use in an endoscope may comprise a proximal valve stem member having a first lumen extending from a proximal opening at a proximalmost end of the proximal valve stem member to a distal opening at a distalmost end of the proximal valve stem member. A distal valve stem member may have a second lumen with a proximal opening at a proximalmost end of the distal valve stem member. The proximalmost end of distal valve stem member may be received within the distal opening of the first lumen. The distal valve stem may be movable relative to the proximal valve stem.

20 Claims, 11 Drawing Sheets

(56) References Cited

FOREIGN PATENT DOCUMENTS

WO   WO-2020039595 A1 *  2/2020   ......... A61B 1/00068

* cited by examiner

MEDICAL VALVE

CROSS-REFERENCE TO RELATED APPLICATIONS

This application claims the benefit of priority from U.S. Provisional Application No. 62/854,689, filed on May 30, 2019, which is incorporated by reference herein in its entirety.

TECHNICAL FIELD

The present disclosure relates generally to valves for medical devices, particularly endoscopes.

BACKGROUND

Endoscopes include functionality to deliver fluids (including air and water) and suction at a site of a procedure. Tubing for delivering fluids and/or suction extends from a handle of the endoscope, through a sheath of the endoscope, and to a distal tip of the endoscope. A combined air/water valve may be used to deliver air or water during the procedure. During a procedure, body fluids, tissues, or other material could enter or build up in the tubing and lead to clogging of the tubing. In order to aid in reprocessing of reusable endoscopes between procedures, pre-processing is performed in an endoscopy suite. For example, water or other fluids are flushed through the tubing after the endoscope is removed from a patient, in order to clear debris from the air/water and/or suction tubing. One option for accomplishing such pre-processing is a reusable cleaning valve. Where reusable air/water and cleaning valves are used, those valves must be subject to reprocessing between procedures. Therefore, a need exists for valves capable of delivering air/water, as well as performing cleaning functions.

SUMMARY

A valve for use in an endoscope may comprise a proximal valve stem member having a first lumen extending from a proximal opening at a proximalmost end of the proximal valve stem member to a distal opening at a distalmost end of the proximal valve stem member. A distal valve stem member may have a second lumen with a proximal opening at a proximalmost end of the distal valve stem member. The proximalmost end of distal valve stem member may be received within the distal opening of the first lumen. The distal valve stem may be movable relative to the proximal valve stem.

Any example of the valves described herein may additionally or alternatively include one or more of the features below. The proximal valve stem member may include a membrane within the first lumen that forms a fluid tight barrier between the proximal opening and the distal opening. In a first configuration, the proximalmost end of the distal valve stem member may be distal to an original location of the membrane so that the first lumen is not in fluid communication with the second lumen. In a second configuration, the membrane may be punctured and the proximalmost end of the distal valve stem may be proximal to the original location of the membrane so that the first lumen is in fluid communication with the second lumen. The distal valve stem member may have a shoulder that is contacted by the distalmost end of the proximal valve stem member in the second configuration. The proximal valve stem member may include a first aperture formed through a wall of the proximal valve stem member. The first aperture may be in fluid communication with the first lumen. The proximal valve stem member may include a second aperture formed through the wall of the proximal valve stem member, and wherein the second aperture is in fluid communication with the first lumen. The second lumen may be closed at a distalmost end of the second lumen. The distal valve stem member may have a third aperture formed through a wall of the distal valve stem member. The third aperture may be in fluid communication with the second lumen. The proximal valve stem member may include a button configured to be contacted by a finger of an operator. A proximal surface of the button may be at the proximalmost end of the proximal valve stem member. The proximal valve stem member may include at least one tab on a distal surface of the button. At least one seal may be disposed on an external surface of the distal valve stem member. At least two O-ring seals may be disposed on an external surface of the distal valve stem member. At least one O-ring seal may be disposed on an external surface of the proximal valve stem member. A one-way seal may be disposed on an external surface of the proximal valve stem member. The proximalmost end of the distal valve stem may be tapered.

In another example, a valve for use in an endoscope may comprise a proximal valve stem member having a first lumen extending from a proximal opening at a proximalmost end of the proximal valve stem member to a distal opening at a distalmost end of the proximal valve stem member. A membrane within the first lumen may form a fluid-tight barrier between the proximal opening and the distal opening. A distal valve stem member may be received within the distal opening of the first lumen. In a first configuration, the proximalmost end of the distal valve stem member may be distal to an original location of the membrane. In a second configuration, the membrane may be punctured and the proximalmost end of the distal valve stem may be proximal to the original location of the membrane. The distal valve stem member may have a second lumen with a proximal opening at a proximalmost end of the distal valve stem member. In the first configuration, the first lumen and the second lumen may not be in fluid communication. In the second configuration, the first lumen and the second lumen may be in fluid communication.

Any example of the valves described herein may additionally or alternatively include one or more of the features below. The second lumen may be closed at a distalmost end of the second lumen. The distal valve stem member may have an aperture formed through a wall of the distal valve stem member. The aperture may be in fluid communication with the second lumen. The proximal valve stem member may include first and second apertures through a wall of the proximal valve stem member. Each of the first and second aperture may be in fluid communication with the first lumen.

A method of delivering air and water may comprise: via a valve to a first configuration, delivering air to an air channel of a medical device; transitioning the valve from the first configuration to a second configuration to deliver water to a water channel of the medical device; and transitioning the valve from the second configuration to a third configuration to deliver the water to the air channel of the medical device.

Any method described herein may include one or more of the features or steps described below. The valve may be transitioned to the first configuration by covering a proximal hole of the valve. Transitioning the valve to the second configuration may include depressing the valve part-way. Transitioning the valve to a third configuration may include fully depressing the valve. The valve may include a proximal valve stem member having a first lumen extending from a proximal opening at a proximalmost end of the proximal valve stem member to a distal opening at a distalmost end of the proximal valve stem member. A membrane within the first lumen may form a fluid-tight barrier between the proximal opening and the distal opening. A distal valve stem member may be received within the distal opening of the first lumen. In the first and second configurations, the proximalmost end of the distal valve stem member is distal to an original location of the membrane. Transitioning from the second configuration to the third configuration may include puncturing the membrane and moving the proximalmost end of the distal valve stem to a position proximal to the original location of the membrane.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to a surface (e.g., a button) contacted by an operator for operating a valve and the term "distal" means a direction away from the surface (e.g., a button) for operating the valve. Although endoscopes are referenced herein, reference to endoscopes or endoscopy should not be construed as limiting the possible applications of the disclosed aspects. For example, the disclosed aspects may be used with duodenoscopes, bronchoscopes, ureteroscopes, colonoscopes, catheters, diagnostic or therapeutic tools or devices, or other types of medical devices.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

A valve may be configured to both deliver air and water during a procedure and to direct a fluid for cleaning air and water channels of an endoscope following the procedure. In embodiments, the valve may be a single-use valve, and therefore disposable after only one procedure and post-procedure, although in other embodiments the valve may be reusable. The valve may have up to four or more configurations. In a first configuration, the valve may deliver neither air nor water to channels in a sheath of the endoscope. In a second configuration, the valve may only deliver air to only an air channel of the sheath. In a third configuration, the valve may deliver only water to only a water channel of the sheath. In a fourth configuration, the valve may deliver only water to both the air and the water channels in order to perform pre-processing cleaning of the air and water channels.

Figure 1A:
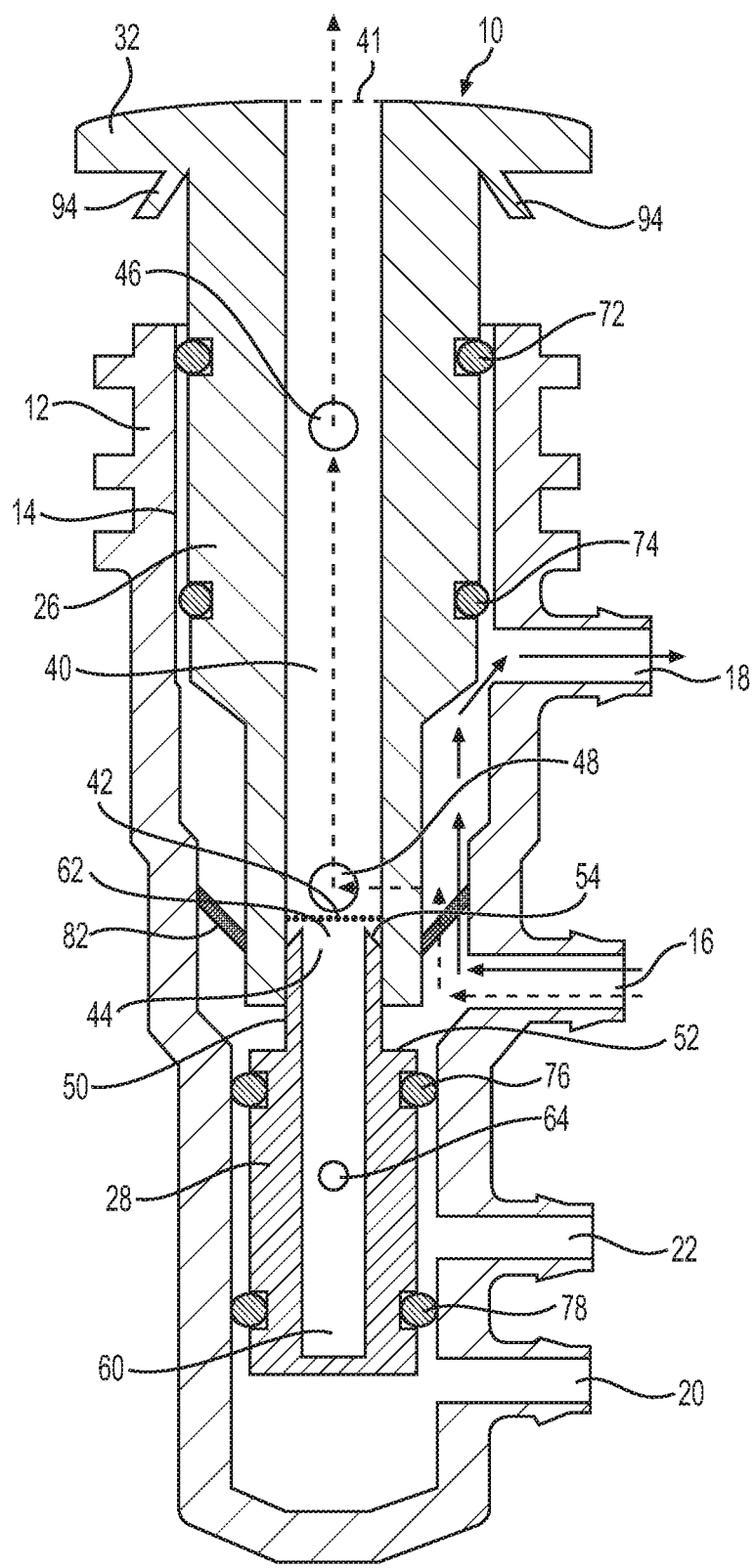
FIGS. 1A-1C show cross-sectional views of a first exemplary valve.
Figure 1B:
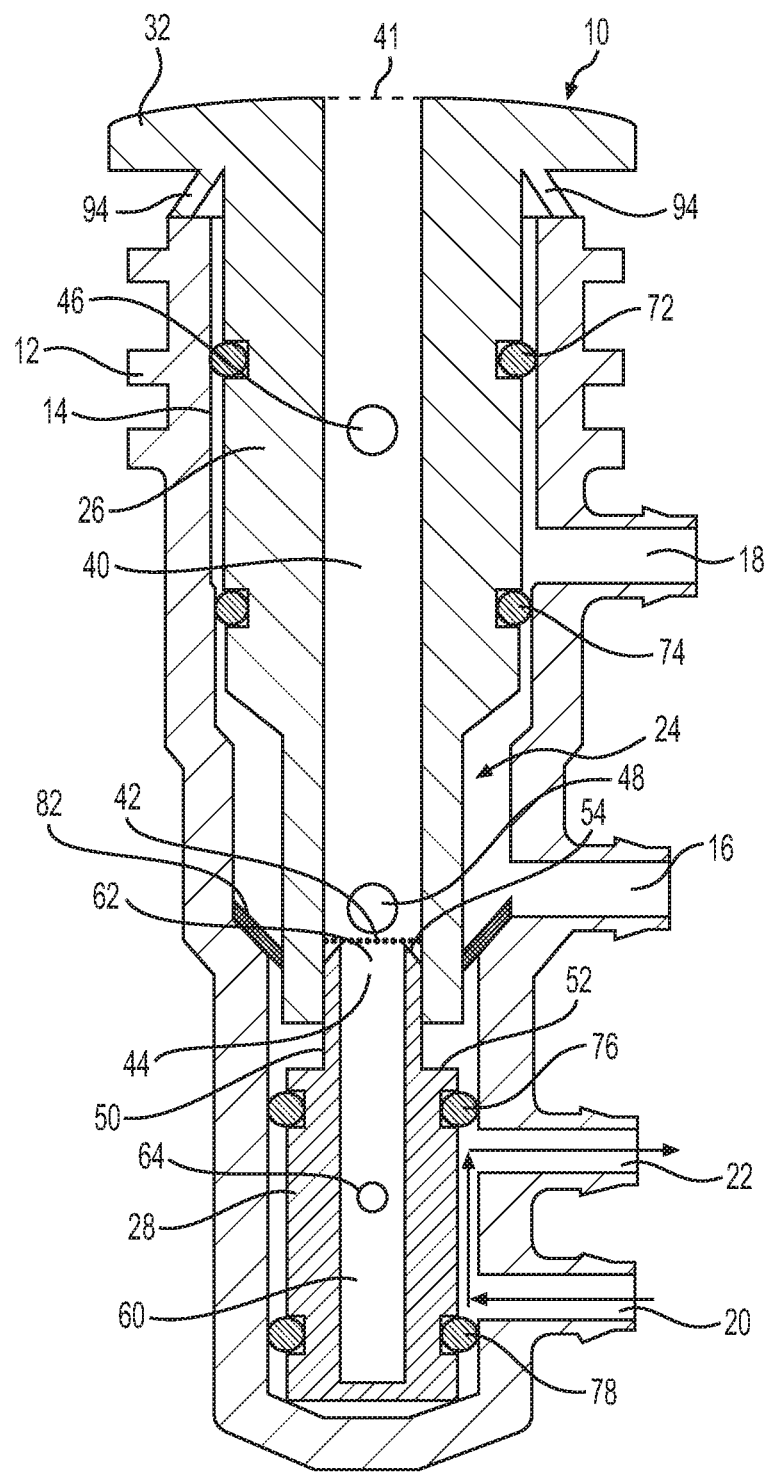
Figure 1C:
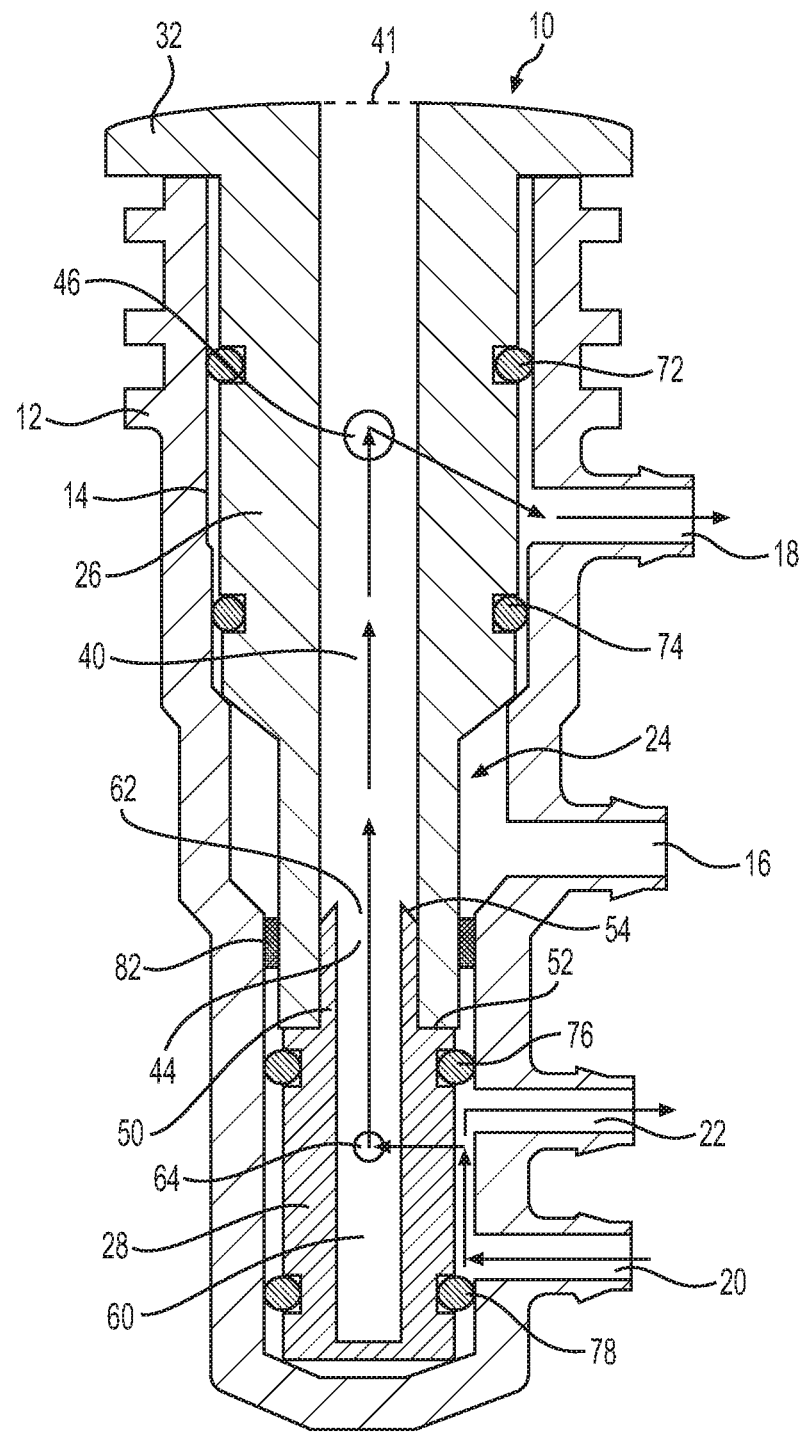

FIGS. 1A-1C show a cross-sectional view of an exemplary valve 10 in a valve cylinder 12. Valve cylinder 12 may have surfaces 14 that define a cavity into which valve 10 may be inserted. Valve cylinder 12 may include connections to channels for inflow or outflow of air or water in a medial device, such as an endoscope. For example, valve cylinder 12 may have an air inlet 16 and an air outlet 18. Valve cylinder 12 may also have a water inlet 20 and a water outlet 22. From proximal to distal, the outlets may be ordered as follows: air outlet 18, air inlet 16, water outlet 22, and water inlet 20.

Valve 10 may have a valve stem 24. Valve stem 24 may have a proximal member 26 and a distal member 28. Portions of valve stem 24 including proximal member 26 and distal member 28, may be made from metal (e.g., stainless steel, titanium, aluminum, etc.), from a polymer (e.g. polycarbonate, ABS, HDPE, Nylon, PEEK, thermoplastic, plastic, etc.), or from any other suitable material. Proximal member 26 and distal member 28 may be made from the same material or from different materials. Proximal member 26 and/or distal member 28 may be formed from a single, continuous material.

Proximal member 26 may include a button 32. Button 32 may be formed as one continuous structure with the rest of proximal member 26, or button 32 may be a separate structure attached to the rest of proximal member 26. Button 32 may have an outer circumference that is wider than a proximal opening of valve cylinder 12, so that when button 32 is depressed, button 32 cannot pass through the proximal opening of valve cylinder 12.

Proximal member 26 may have a proximal lumen 40. Proximal member 26 may have a generally annular shape around lumen 40. Proximal lumen 40 may have a proximalmost opening 41 on a proximalmost end of proximal member 26. For example, proximal lumen 40 may be open on a proximalmost side of button 32. Proximal opening 41 is shown with dashes to indicate that, as discussed below, proximal opening 41 may be covered by an operator (e.g., by the finger or thumb of an operator).

As shown in FIGS. 1A and 1B, a membrane 42 may extend completely across proximal lumen 40 toward a distal end 44 of proximal lumen 40. For example, membrane 42 may be a small distance from a distalmost end of proximal lumen 40. Alternatively, membrane 42 may be at a distalmost end of proximal lumen 40. Membrane 42 may be formed of a thin material. Aspects of membrane 42 will be discussed in further detail with reference to FIGS. 1B-1C.

A proximal aperture 46 may be formed in, and extend completely through, a wall of proximal member 26 and may fluidly connect proximal lumen 40 to an area external to proximal member 26. Although one proximal aperture 46 is shown in FIGS. 1A-1C, any number of proximal apertures may be used. One or more air apertures 48 may also be formed in, and extend completely through, a wall of proximal member 26 and may fluidly connect proximal lumen 40 to an area external to proximal member 26. Although only one air aperture 48 is shown, any suitable number of apertures may be utilized.

Distal member 28 may include a neck 50 on a proximal end of distal member 28. Neck 50 may have an outer diameter that is smaller than a diameter of lumen 40. Neck 50 may terminate distally in a shoulder 52. Neck 50 may have a proximal tapered portion 54. A distal lumen 60 may pass through distal member 28, including neck 50. Distal lumen 60 may be open on a proximalmost side of distal member 28 (e.g., on a proximalmost end 62 of neck 50) and may be closed on a distalmost side of distal member 28. A diameter of distal lumen 60 may be smaller than a diameter of proximal lumen 40. Tapered portion 54 may taper from an initial outer diameter (at a proximal end) until its outer diameter is substantially the same as a diameter of distal lumen 60. The proximalmost end of tapered portion 54 may form a sufficiently sharp annular ring to cut through, puncture, or otherwise remove membrane 42 under sufficient force. Portions of membrane 42 that are severed by tapered portion 54 may be flushed away by fluids flowing through valve 10 (further details of the flushing process are discussed below) or may remain within valve 10. A distal aperture 64 may be formed in, and extend completely through, a wall of distal member 28 and may fluidly connect distal lumen 60 to an area external to distal member 28. Although one distal aperture 64 is shown in FIGS. 1A-1C, any number of distal apertures may be used.

Neck 50 may be slidably received within proximal lumen 40 so that distal lumen 60 is in fluid communication with proximal lumen 40. Proximal lumen 40 and/or neck 50 may have features (e.g., indentations, protrusions, tabs, etc.) (not shown) that retain neck 50 within lumen 40 and prevent a proximalmost end 62 of neck 50 from exiting a distalmost end 44 of proximal lumen 40.

Valve stem 30 may be fitted with one or more seals. For example, valve stem 30 may include, in a direction from proximal to distal, a first seal 72, a second seal 74, a third seal 76, and a fourth seal 78. Seals 72, 74, 76, and 78 may be, for example, O-rings. Seals 72, 74, 76, and 78 may be formed from an elastomeric material. Valve stem 30 may also include a one-way seal 82, which may be made of the same or different material as seals 72, 74, 76, and 78 (e.g., an elastomeric material). One-way seal 82 may permit passage of fluid or other substances proximally past one-way seal 82 but may not permit passage of fluid or other substances distally past one-way seal 82 due to its flexibility and arrangement relative to its contacted structure. First seal 72 and second seal 74 may be disposed on proximal member 26. Third seal 76 and fourth seal 78 may be disposed on distal member 28. One-way seal 82 may be disposed on proximal member 26 between second seal 74 and third seal 76. Alternatively, seals 72, 74, 76, 78 and one-way seal 82 may be disposed on alternative portions of valve stem 30 or in different orders. Proximal aperture 46 may be disposed between first seal 72 and second seal 74. Distal aperture 64 may be disposed between third seal 76 and fourth seal 78.

Seals 72, 74, 76, and 78 may be configured so as to form a slidable interference fit between seals 72, 74, 76, and 78 and surface 14. Thus, valve stem 30 can move relative to surface 14, but fluids (e.g. water and air) cannot move between seals 72, 74, 76, and 78 and surface 14. Thus, seals 72, 74, 76, and 78 prevent movement of fluids external to valve 10 in a proximal or distal direction past seals 72, 74, 76, and 78.

An inner diameter of one-way seal 82 may be sized so that there is a slight interference between an external surface of proximal member 26 and the inner diameter of one-way seal 82, so that a tight seal is formed. An outer diameter of one-way seal 82 may be sized so as to form a slight interference fit with a portion of surface 14. A thin flap of one-way seal 82 may extend radially outward from proximal member 26 at an angle transverse to a longitudinal axis of proximal member 26. For example, the thin flap may extend at an angle between 10 degrees and 80 degrees relative to a longitudinal axis of proximal member 26. The flap of one-way seal 82 may be expandable so that when fluid (e.g., water or air) moves in a distal direction toward one-way seal 82, a positive pressure will expand the flap, maintaining a seal between one-way seal 82 and surface 14. Fluid moving proximally toward one-way seal 82 will also create a positive pressure, but the positive pressure will produce a force normal to a longitudinal axis of proximal member 26 to radially compress the flap of one-way seal 82. Thus, fluid (e.g., air or water) is permitted to move proximally past one-way seal 82, between one-way seal 82 and surface 14.

FIG. 1A shows valve 10 in a first configuration and/or a second configuration. In the first configuration of valve 10, neither air nor water is delivered to any outlets of valve 10 and will vent through proximalmost opening 41 to the atmosphere.

In the second configuration, air is delivered to an air channel of an endoscope but water is not delivered to any channel. The first configuration and second configuration may differ only in that proximalmost opening 41 at a proximalmost end of proximal lumen 40 is left open in the first configuration and is blocked (e.g., by an operator's thumb or finger) in the second configuration. In the first and second configurations, button 32 may not be pushed down. Valve 10 may include features such as tactile feedback features (not shown) to indicate that valve 10 is in a proper position within valve cylinder 12. For example, valve 10 can include ridges, bumps, or other protrusions on an outside surface of proximal member 26. Proximalmost end 62 of distal lumen 60 (and neck 50) may be distal of membrane 42 so that proximal lumen 40 is not in fluid communication with distal lumen 60.

In the first and second configurations, water inlet 20 may be distal to fourth seal 78. Water outlet 22 may be between third seal 76 and fourth seal 78. Thus, water from water inlet 20 may not move proximally of fourth seal 78. Water outlet 22 is surrounded by third seal 76 and fourth seal 78, and therefore fluids (air and water) cannot move longitudinally to water outlet 22 along surfaces 14 of cylinder 12. And because membrane 42 is in place, distal lumen 60 and proximal lumen 40 are not in fluid communication. Thus, no fluids may exit water outlet 22.

In the first configuration (e.g., when proximalmost opening 41 is not covered and neither air nor water is delivered), as shown in dashed-line arrows on FIG. 1A, air may enter from air inlet 16, pass proximally past one-way seal 82, and then pass around a circumference of proximal member 26 of valve stem 24 to air aperture 48. Air will enter air aperture 48 instead of passing out air outlet 18 because proximalmost opening 41 venting to the atmosphere provides the path of least resistance. Air may then vent proximally out of proximalmost opening 41. Any air that would exit aperture 46 would be trapped between first seal 72 and second seal 74, so air will instead vent from proximalmost opening 41. Air may not travel distally past third seal 76 and thus may not exit water outlet 22. Air inlet 16 may be proximal of third seal 76 but distal to one-way seal 82. Though air entering from air inlet 16 could travel proximally past one-way seal 82 toward air outlet 18, the path of least resistance will be for air to vent from proximalmost opening 41, and therefore air will not exit air outlet 18. Thus, in the first configuration, neither air nor water is delivered.

In the second configuration, also shown in FIG. 1A, proximalmost opening 41 may be covered by, for example, an operator's thumb or finger. Proximalmost opening 41 may also be covered in the third and fourth configurations, discussed below. Otherwise, the second configuration may be identical to the first configuration, e.g., all of the structures of valve 10 are in the same locations relative to one another and cylinder 12. Because air can no longer vent out of proximalmost opening 41, as shown in solid-line arrows on FIG. 1A, air entering from air inlet 16 may travel proximally past one-way seal 82. Thus, air entering from air inlet 16 may pass through air outlet 18 to deliver air to an air channel of an endoscope. Air from air inlet 16 may not pass proximally of second seal 74 and thus may not enter proximal aperture 46. air entering aperture 48 cannot exit proximalmost opening 41 as it is covered. Thus, in the second configuration, valve 10 will deliver air to an air channel of the endoscope.

FIG. 1B shows valve 10 in a third configuration, in which water is delivered to a water channel of the endoscope but air is not delivered to any endoscope channel. To transition from the second configuration to the third configuration, button 32 may be depressed part-way. For example, button 32 may be depressed until a pliable feature on a distal surface of button 32 is in contact with an outer, proximal surface of cylinder 12. For example, tabs 94 may contact an outer surface of cylinder 12. Contact of features such as tabs 94 may cause tactile feedback to an operator to indicate that valve 10 is in the third configuration. Tabs 94 are merely exemplary, and any suitable feature may be used. For example, an annular flap/flange, expanded inflatable features, frangible piece, or other feature may be used. Tabs 94 may be made of the same material as button 32 or from a different material.

In transitioning from the second configuration to the third configuration, both proximal member 26 and distal member 28 may translate distally relative to cylinder 12, as a result of button 32 being pressed downward. Membrane 42 may be sufficiently resilient that a force on button 32 to transition valve 10 from the second configuration to the third configuration may not cause a proximalmost end of neck 50 to break through membrane 42. Therefore, membrane 42 may remain intact in the third configuration, and a force on neck 50 from membrane 42 may cause a distal translation of distal member 28 along with proximal member 26. Distal member 28 (and proximal member 26) may translate distally until distal member 28 rests on a distal surface of cylinder 12, or until tabs 94 contact an upper, proximal surface of cylinder 12. Additionally or alternatively, a frictional force between an outer surface of neck 50 and an inner surface of proximal lumen 40 may cause distal member 28 to move in unison with proximal member 26.

In the third configuration, fourth seal 78 may be distal to water inlet 20. Third seal 76 may be proximal of water outlet 22. Thus, as shown in solid-line arrows, water from water inlet 20 may not move distally past fourth seal 78 but may move through water outlet 22 and through a water channel of an endoscope. Although water may move through distal aperture 64, water may not move proximally past membrane 42, which may be resilient enough to block proximal movement of water. Thus, water may not enter proximal lumen 40. Water also may not move proximally past third seal 76. One-way seal 82 may be distal to air inlet 16 so air can not pass to enter air aperture 48. Second seal 74 may be proximal of air inlet 16. Thus, air from air inlet 16 may not move into proximal lumen 40 through air aperture 48 or past seal 74, thus will not exit air outlet 18. And, because an operator's finger or thumb still covers proximalmost opening 41, air cannot enter air aperture 48 and vent from proximalmost opening 41. As a result, in the third configuration, the only fluid flow to the endoscope sheath is that of water through the water channel.

Valve 10 may be transitioned from the third configuration back to the first/second configuration. For example, valve 10 may have a spring (not shown) or other feature which biases valve 10 to the first configuration. Alternatively, valve 10 may be transitioned from the third configuration (or the first/second configuration) to the fourth configuration.

As shown in FIG. 1C, the fourth configuration facilitates flushing of water from water inlet 20 through both water outlet 22 and air outlet 18. The fourth configuration may be referred to as the cleaning configuration of valve 10. To move from the third configuration to the fourth configuration, button 32 may be depressed until tabs 94 are collapsed against a surface of cylinder 12. Substantially more force may be required to transition valve 10 to the fourth configuration than to the third configuration. While button 32 is depressed part-way in the third configuration, button 32 may be fully depressed in the fourth configuration. In the fourth configuration, tabs 94 may break (e.g., by cracking off at a proximal end of tabs 94) or bend flat so as to be parallel with a proximal surface of button 32 and/or a proximal surface of endoscope cylinder 12. A certain, minimum amount of force may be required to bend or break tabs 94.

Because distal member 28 already rested on a distal surface of cylinder 12 in the third configuration, distal member 28 may not translate distally along with proximal member 26 when button 32 is depressed fully. Translation of proximal member 26 distally relative to distal member 28 may cause proximal tapered portion 54 to pierce membrane 42 and thereby fluidly connect distal lumen 60 and proximal lumen 40. In the fourth configuration, proximal tapered portion 54 of distal member 28 may be proximal of the original location of membrane 42. Therefore, as shown with solid-line arrows, in the fourth configuration of valve 10, water may travel from water inlet 20 and out of water outlet 22, as in the third configuration of valve 10. However, unlike the third configuration, the fourth configuration also permits water to travel into proximal aperture 64, through distal lumen 60, into proximal lumen 40, and out of proximal aperture 46, so that water may flow between valve stem 30 and a surface of valve cylinder 12 to air outlet 18. Because air aperture 48 may be covered by neck portion 50 in the fourth configuration, water may not pass through air aperture 48.

The fourth configuration should not be used while an endoscope is inside of a body lumen of a patient. Valve 10 may contain mechanisms to prevent an operator from unintentionally transitioning valve 10 to the fourth configuration. For example, tabs 94 may provide resistance or other tactile feedback against pushing down button 32 past the third configuration. An operator may also receive tactile feedback from a distal end of distal member 28 contacting a distal surface of valve cylinder 12 in the third configuration, indicating to the operator that button 32 should not be further depressed while an endoscope is in use during a patient procedure. Additionally or alternatively, other methods may be used to prevent accidental transition of valve 10 into the fourth configuration. For example, a deformable mechanical stop may provide audible feedback (e.g., a "click" sound), valve 10 could require rotation prior to transitioning to the fourth configuration, and/or a visual indicator may provide feedback to an operator.

Because membrane 42 is broken in the fourth configuration, valve 10 may not again be used in any of the first, second, or third configurations. Therefore, valve 10 is a single-use valve, for use during only one pre-processing cleaning step. Alternatively, after use in one pre-processing cleaning, valve 10 could be used as only a pre-processing cleaning valve 10 without use during patient procedures. Alternatively, membrane 42 may be a strong, reusable seal that could be reset following use so that valve 10 is reusable over multiple procedures.

In order to make use of valve 10, an operator may insert valve 10 into valve cylinder 12 of an endoscope prior to a procedure. During the procedure, the operator may use valve 10 in the first, second, and/or third configurations, depending on the operator's desire to make use of air or water during the procedure. Following the procedure, the endoscope may be removed from the patient for reprocessing. Button 32 may be fully depressed so that valve 10 transitions to the fourth configuration. Valve 10 may flush water through the air and water channels for a predetermined amount of time (e.g., thirty seconds). After flushing is complete, an operator could either move button 32 proximally to disable the flow of water or could simply remove valve 10 from valve cylinder 12. Alternatively, button 32 may automatically move proximally to disable the flow of water. The endoscope would be subject to further reprocessing, and valve 10 may be disposed.

Figure 2A:
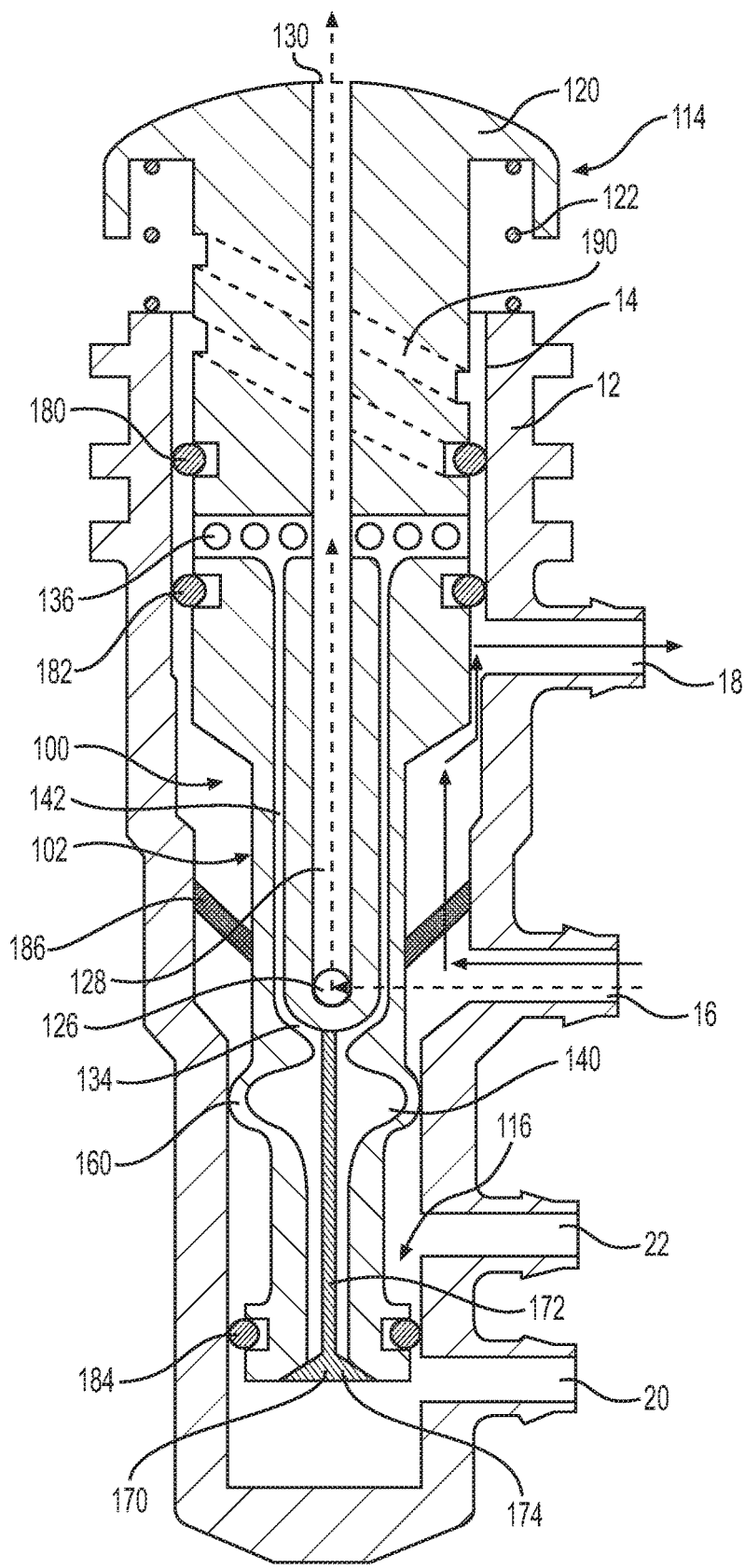
FIGS. 2A-2C show cross-sectional views of a second exemplary valve.
Figure 2B:
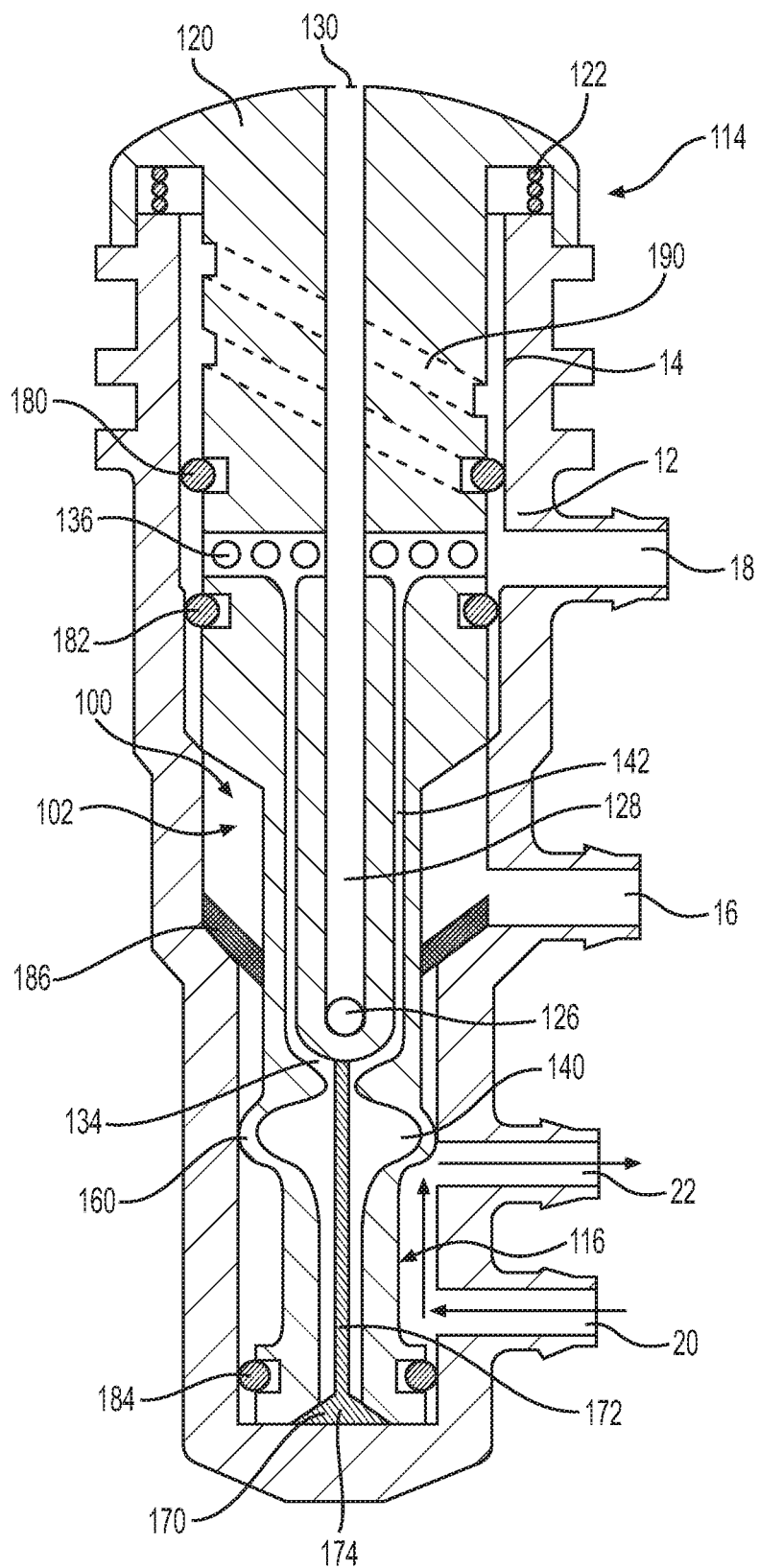
Figure 2C:
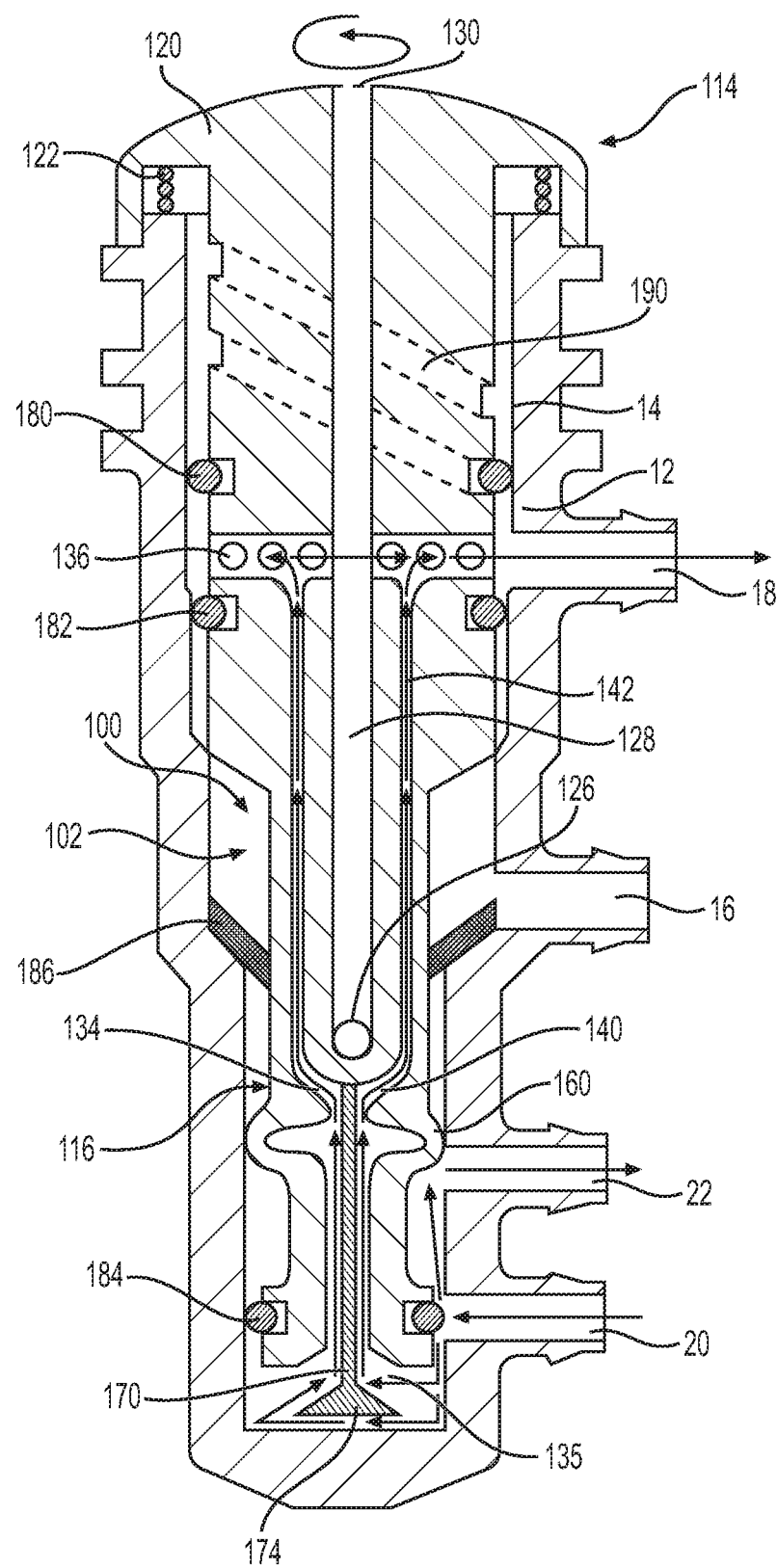

FIGS. 2A-2C depict configurations of another exemplary valve 100. Although the same valve cylinder 12 is referenced herein, it will be understood that valve 100 may be used in a different valve cylinder. FIG. 2A shows valve 100 in a first/second configuration, FIG. 2B shows valve 100 in a third configuration, and FIG. 2C shows valve 100 in a fourth configuration. Valve 100 may have a valve stem 102. Valve stem 102 may have a proximal portion 114 and a distal portion 116. Proximal portion 114 of valve stem 102 may include a button 120, which may be configured to be contacted by a finger of an operator in use of valve 100. A spring 122 may be disposed in an annular groove within button 120 and against a distally-facing surface of button 120. When valve 100 is inserted into cylinder 12, a distal surface of spring 122 may rest upon a proximal surface of cylinder 12.

Valve stem 102 may have an air release lumen 128. Air release lumen 128 may extend through button 120 and have a proximalmost opening 130 on a proximal surface of button 120. Proximalmost opening 130 is shown with dashed lines to indicate that proximalmost opening 130 may be covered by an operator (e.g., by a thumb/finger of an operator). A distal end of air release lumen 128 may be open to an exterior surface of valve stem 102 via an air aperture 126, so that air release lumen 128 is in fluid communication with an area exterior to valve stem 102. Air release lumen 128 may extend through a longitudinal axis of valve stem 102, such as a central longitudinal axis of valve stem 102.

Valve stem 102 may also have a water lumen 134. Water lumen 134 may extend to a distalmost end of valve stem 102 and may have a distalmost opening 135 (see FIG. 2C). Water lumen 134 may have one or more water apertures 136. Water apertures 136 may be a plurality of openings on a circumferential surface of valve stem 102. Water lumen 134 may be in fluid communication with an area exterior to valve stem 102 via water apertures 136. Water lumen 134 may have a distal portion 140 that is below (distal to) air aperture 126 and that extends along a central longitudinal axis of valve stem 102. At a point distal to a distalmost end of air release lumen 128, water lumen 134 may divert from a central longitudinal axis of valve stem 102. A proximal portion 142 of water lumen 134 may extend along a longitudinal axis of valve stem 102 that is off-centered. As shown in FIG. 2A, proximal portion 142 of water lumen 134 may include a plurality of branches radially outward of a central longitudinal axis of valve stem 102 (e.g., two branches). Alternatively, a proximal portion 142 of water lumen 134 may extend annularly about air release lumen 128. Each branch of proximal portion 142 of water lumen 134 may be in communication with a separate plurality of apertures 136. Alternatively, apertures 136 may extend circumferentially around proximal portion 142 so that branches of proximal portion 142 share access to a set of apertures 136.

A collapsible seal 160 may form an annular wall of valve stem 102 and may surround a part of distal portion 140 of water lumen 134. Collapsible seal 160 may be formed of the same material as a remainder of valve stem 102 or from a different material. Collapsible seal 160 may be a single, unitary structure with the remainder of valve stem 102. Alternatively, collapsible seal 160 may include separate or additional structures from the remainder of valve stem 102. In certain examples, material of a remainder of valve stem 102 (apart from collapsible seal 160) may be discontinuous at a location of collapsible seal 160, and collapsible seal 160 may be bonded to a proximal and distal portion of valve stem 102 bordering collapsible seal 160. For example, collapsible seal 160 may be made of a flexible polymer (e.g., TPE) having appropriate properties (such as an appropriately high durometer value). Collapsible seal 160 may be bonded to portions of distal portion 116 of valve stem 102 proximal and distal of collapsible seal 160 using, for example, adhesive or another suitable method. Alternatively, a thin cylinder of metal may extend through a center of collapsible seal 160, and collapsible seal 160 may be bonded to the thin cylinder of metal. The cylinder of metal and/or collapsible seal 160 may be bonded to portions of distal portion 116 of valve stem 102 proximal and distal of collapsible seal 160. The thin cylinder of metal may have an interior lumen that is in fluid communication with the rest of water lumen 134. Exemplary collapsible seals 160 are discussed in further detail below, with respect to FIGS. 3A-3B and 4A-4B. A poppet valve 170 may extend within water lumen 134 and may have a proximal end at a distal inner surface of distal portion 140 distal of water lumen 134. Poppet valve 170 may include a shaft 172 and a tapered plug 174. Further functionality of poppet valve 170 will be described below. Shaft 172 may be fixedly attached to valve stem 102. When a distal portion 116 of valve stem 102 is in the first, second, and third configurations, tapered plug 174 may be seated against distal portion 116, creating a seal between mating surfaces of poppet valve 170 and distal portion 116. When distal portion 116 of valve stem 102 Is in the fourth configuration, distal portion 116 is displaced proximally and moves away from tapered plug 174. This displacement opens distalmost opening 135 of water lumen 134 to water inlet 20 and water outlet 22.

Valve stem 102 may also be fitted with a plurality of seals. For example, valve stem 102 may include a first seal 180, a second seal 182, and a third seal 184. Seals 180, 182, and 184 may be disposed in grooves of valve stem 102. Seals 180, 182, and 184 may have any of the properties of seals 72, 74, 76, or 78, described above. Seals 180, 182, and 184 may have a slidable interference fit with a surface 14 of valve cylinder 12 so that fluids (e.g., air, water) cannot move proximally or distally between seal 180, 182, or 184 and the surface 14 of valve cylinder 12. First seal 180 may be disposed proximally of water apertures 136. Second seal 182 may be disposed distally of water apertures 136 and proximally of air aperture 126. Third seal 184 may be disposed distally of air aperture 126 and collapsible seal 160. Valve stem 102 may also have a one-way seal 186 that may have any of the properties of one-way seal 82. One-way seal 186 may permit fluids (e.g., air and water) to move proximally past one-way seal 82 but not distally past one-way seal 186.

Valve stem 102 may also include a plurality of coarse threads 190. Coarse threads 190 are shown in dashed lines in FIGS. 2A-2C because they may be on a circumferential outer surface of valve stem 102. Coarse threads 190 may include alternative indentations and protrusions.

FIG. 2A shows valve 100 in a first and/or second configuration. In the first and second configurations, button 120 may not be depressed and spring 122 may be in a relaxed, extended state. Spring 122 may be biased to the configuration of FIG. 2A. First and second seals 180, 182 may be proximal to air outlet 18. One-way seal 186 may be between air outlet 18 and air inlet 16. Collapsible seal 160 may be between air inlet 16 and water outlet 22. Third seal 184 may be proximal of water inlet 20 and distal to water outlet 22. Poppet valve 170 may be closed (plug 174 closes opening 135) so that fluid cannot enter a distalmost opening 135 of water lumen 134.

In a first configuration, proximalmost opening 130 may be left uncovered. Water from water inlet 20 may not move proximally past third seal 184. Water from water inlet 20 may also not enter water lumen 134 because poppet valve 170 is closed. Therefore, water cannot exit into channels of the endoscope. As shown with dashed-line arrows, air from air inlet 16 will be drawn to air aperture 126, through air release lumen 128 and out of proximalmost opening 130. Air will be drawn to enter air aperture 126 instead of passing proximally of one-way seal 186 because air aperture 126 and proximalmost opening 130 provide the path of least resistance, as there is no resistance for the air to exit to atmospheric pressure. Therefore, when proximalmost opening 130 is uncovered, air incoming from air inlet 16 does not have sufficient pressure to bypass flexible seal 186.

In a second configuration, air may be delivered to a body lumen of a patient during a procedure. In the second configuration, proximalmost opening 130 may be covered by, for example, a thumb or finger of an operator. Proximalmost opening 130 may also be covered in the third and fourth configurations, discussed below. Thus, as shown in solid-line arrows, air will be prevented from exiting proximalmost opening 130. Instead, air from air inlet 16 will travel proximally past one-way seal 186 and out air outlet 18. Air may not travel proximally past second seal 182 and may thus not exit a proximal opening of cylinder 12.

To transition valve 100 to a third configuration, button 120 may be pressed distally, compressing spring 122 and moving valve stem 102 distally. In the third configuration, poppet valve 170 remains closed (plug 174 remains covering opening 135). Shaft 172 of poppet valve 170 may be fixedly attached to valve stem 102 at a proximal end of shaft 172. Collapsible seal 160 may be sufficiently stiff along an axial/longitudinal direction so as to enable movement of valve stem 102 as a unit (including distal portion 116 of valve stem 102). First seal 180 is proximal of air outlet 18, while second seal 182 is distal to air outlet 18. Third seal 184 may be distal to water inlet 20, one-way seal 186 may be distal to air inlet 16 and proximal of water outlet 22, and collapsible seal 160 may be proximal of water outlet 22. Therefore, as shown in solid-line arrows, water may enter from water inlet 20 and pass out of water outlet 22, as no seals are between water inlet 20 and water outlet 22. However, water cannot move proximally past collapsible seal 160. Air from air inlet 16 may not move proximally of second seal 182 or one-way seal 186 to enter air aperture 126. Thus, although proximalmost opening 130 may be covered by a finger or thumb of an operator, air may not exit air outlet 18. Air may likewise not exit water outlet 22 because air cannot travel distally from air inlet 16 past one-way seal 186.

Valve 100 may be transitioned back to the first or second configuration by releasing pressure on button 120. Spring 122 may be biased to an expanded state of the first configuration. Thus, button 120 may move proximally to the position of the first/second configurations when button 120 is released.

To transition valve 100 to a fourth configuration, button 120 (and valve stem 102) may be rotated in a counter-clockwise direction, which may engage coarse threads 190 and cause a distal portion 116 of valve stem 102 to be pulled upward. Coarse threads 190 may be operative (via, e.g., an internal mechanism) to pull upward on distal portion 116 of valve stem 102. Upward motion of distal portion 116 may cause collapsible seal 160 to collapse. Collapse of collapsible seal 160 may cause poppet valve 170 to open (unseat from opening 135). In an alternative embodiment, rotating button 120 may open a valve that ports air pressure from air inlet 16 to a distalmost chamber in valve 100, distal to poppet valve 170 and the distal portion 116 of valve stem 102. This action may drive the distal portion 116 of valve stem 102 proximally, compressing collapsible seal 160 and opening water channel 134 to water inlet 20. Alternatively to poppet valve 170, a porous elastomer seal may be used. When the porous elastomer is relaxed (e.g., in configurations 1-3 of FIGS. 2A and 2B), the pores may be closed, and fluid may not pass the porous seal. When the seal is stretched, such as in the fourth configuration of FIG. 2C, the pores will be opened and fluids such as water may pass through the porous elastomer seal.

In the fourth configuration, third seal 184 may be aligned with water inlet 20. Collapsible seal 160 may remain proximal of water outlet 22. One-way seal 186 may remain distal to air inlet 16, and second seal 182 may remain distal to air outlet 18. First seal 180 may be proximal of air outlet 18. Thus, as shown in solid-line arrows, water from water inlet 20 may move distally toward distalmost opening 135 of water lumen 134. Because poppet valve 170 is open, water may enter water lumen 134 and travel proximally through water lumen 134 and through water apertures 136. Water may then move between an outer circumference of valve stem 102 and a surface of valve cylinder 12 and out air outlet 18. Water may also move proximally of water inlet 20 and to water outlet 22. Thus, in the fourth configuration, water may flush the air and water channels of an endoscope.

Collapsing of collapsible seal 160 may be a non-reversible process. Thus, after collapsible seal 160 is transitioned to the fourth configuration, it may not be transitioned back to the first, second, or third configuration.

In order to make use of valve 100, an operator may insert valve 100 into valve cylinder 12 of an endoscope prior to a procedure. During the procedure, the operator may use valve 100 in the first, second, and/or third configurations, depending on the operator's desire to make use of air or water during the procedure. Following the procedure, after the endoscope is removed from the patient for reprocessing, button 120 may be rotated so that valve 100 transitions to the fourth configuration. Valve 100 may flush water through the air and water channels for a predetermined amount of time (e.g., thirty seconds). After flushing is complete, an operator could shut off an air and water supply to disable the flow of air and water or could simply remove valve 100 from valve cylinder 12. The endoscope would be subject to further processing, and valve 100 would be disposed.

Figure 3B:
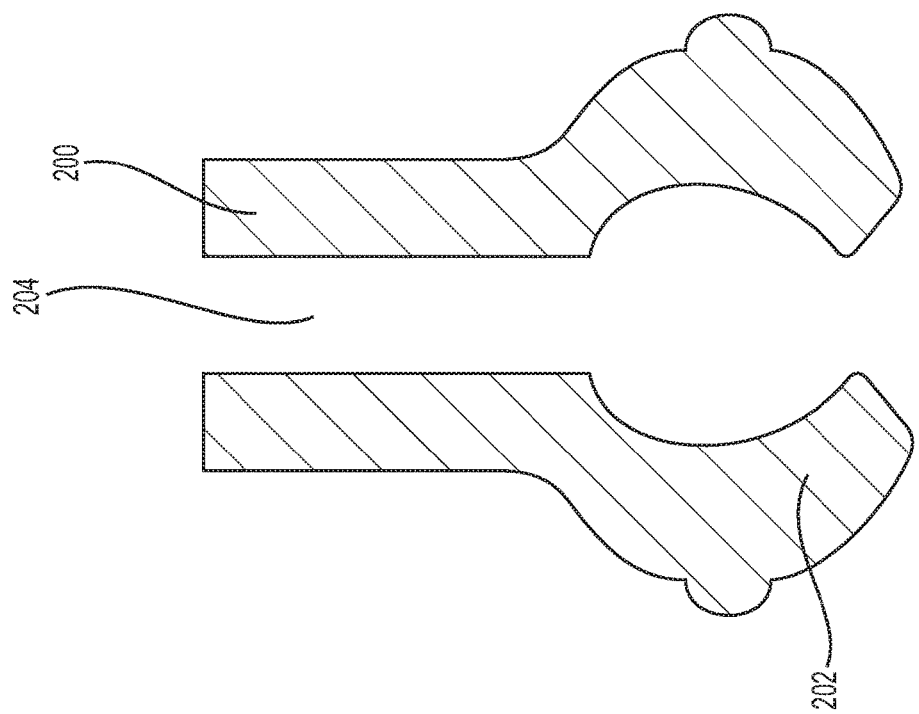
FIGS. 3A-3B and 4A-4B show exemplary seals for use with the second exemplary valve.
Figure 3A:
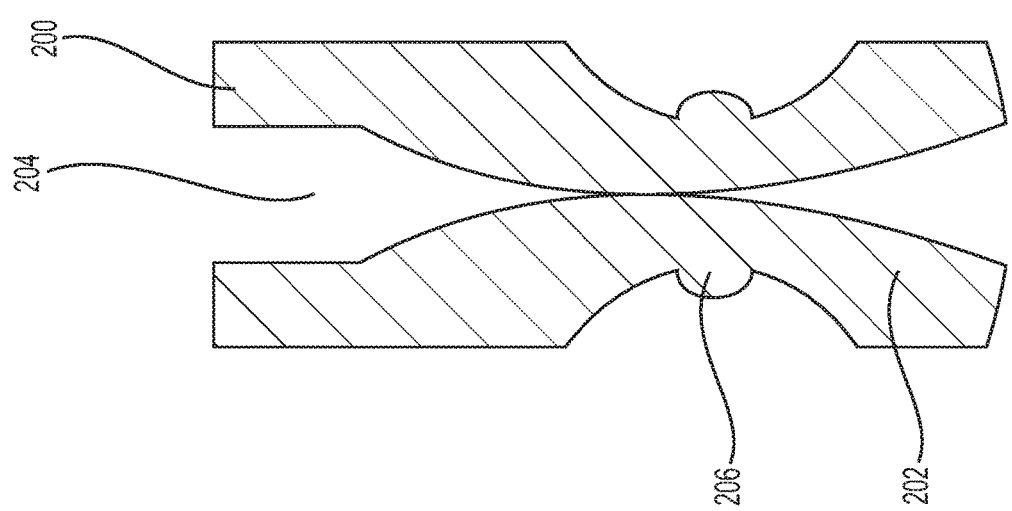

FIGS. 3A and 3B show an exemplary first collapsible seal 200, which may be used with valve 100. Collapsible seal 200 may be constructed of a flexible material, such as an elastomeric material or flexible polymer such as TPE. FIG. 3A shows collapsible seal 200 in a first, closed configuration. FIG. 3B shows collapsible seal 200 in a second, open configuration. In the closed configuration of FIG. 3A, an annular wall 202 of collapsible seal 200 projects inward into a central lumen 204 of collapsible seal 200. Contact between annular walls 202 in central lumen 204 prevents fluid (e.g., water) from passing through central lumen 204.

Collapsible seal 200 may be transitioned to the open configuration by inflating valve 200 using a fluid such as water or air. Air may be ported from air inlet 16 and actuated by a twist or push motion on the proximal end of a valve employing collapsible seal 200. In the second configuration, wall 202 of collapsible seal 200 expands so that inner surfaces of wall 202 may be separated from one another and so that central lumen 204 is open and passible to fluid such as water. A circumferential outer surface of wall 202 may have a feature 206 (e.g., a protrusion), which causes walls 202 to engage with an inner surface of cylinder 12 and to block flow of fluid proximally past an outer surface of collapsible seal 200.

Figure 4A:
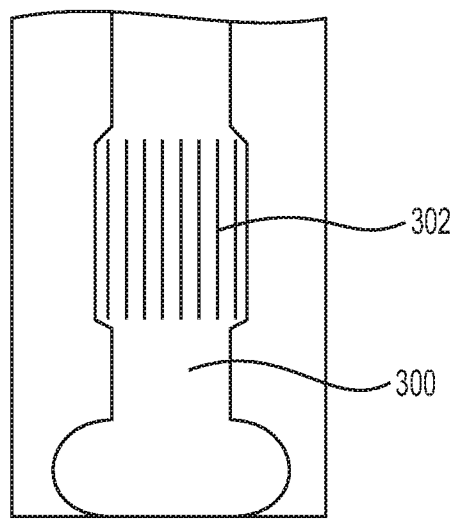
Figure 4B:
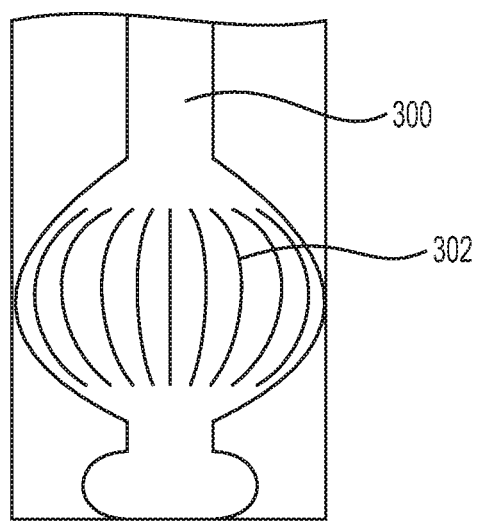

FIGS. 4A and 4B show another exemplary collapsible seal 300. Collapsible seal 300 may be formed of a rigid or semi-rigid material such as plastic or metal. Collapsible seal 300 may have a plurality of longitudinal slots 302 formed around a circumferential surface of collapsible seal 300. Longitudinal slots 302 may be covered by a material such as an elastomer (not shown) to make them impervious to fluids such as water and air. In the first configuration of collapsible seal 300, shown in FIG. 4A, an outer surface of collapsible seal 300 including slots 302 may be relatively parallel with a longitudinal axis of collapsible seal 300.

In FIG. 4B, collapsible seal 300 has transitioned to a second configuration via, e.g., the mechanisms described above for transitioning valve 100 to the fourth configuration of FIG. 2C. In the second configuration, an annular wall of collapsible seal 300 bulges outward due to flexibility imparted by slots 302. An exterior, circumferential surface of the wall of collapsible seal 300 may make contact with the walls of valve cylinder 12, barring passage of fluid, such as water, proximally past an exterior of collapsible seal 300. However, fluids such as water may travel proximally through a distal opening of collapsible seal 300 and through a central lumen of collapsible seal 300.

Figure 5A:
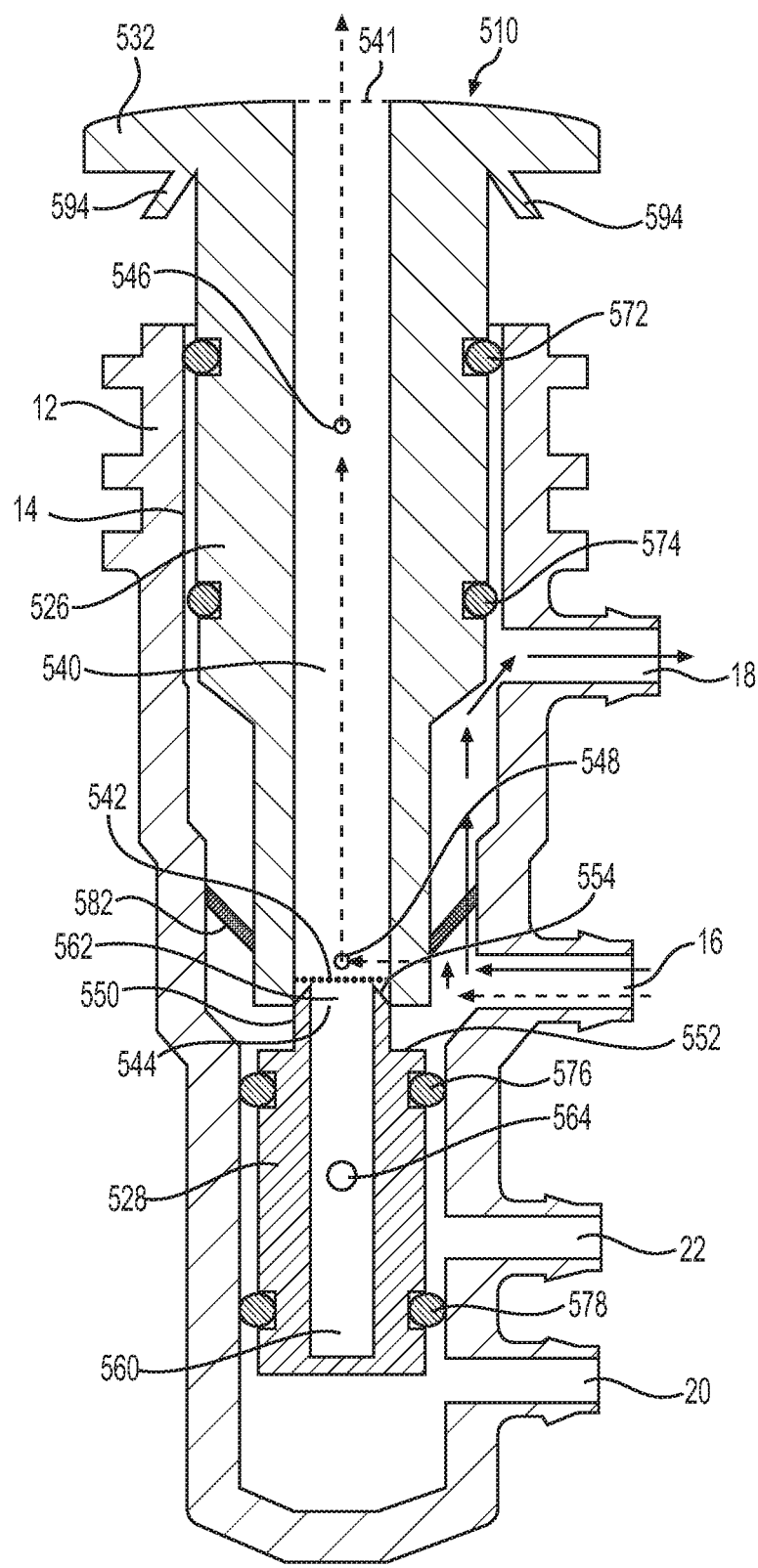
FIGS. 5A-5C show cross-sectional views of a third exemplary valve.
Figure 5B:
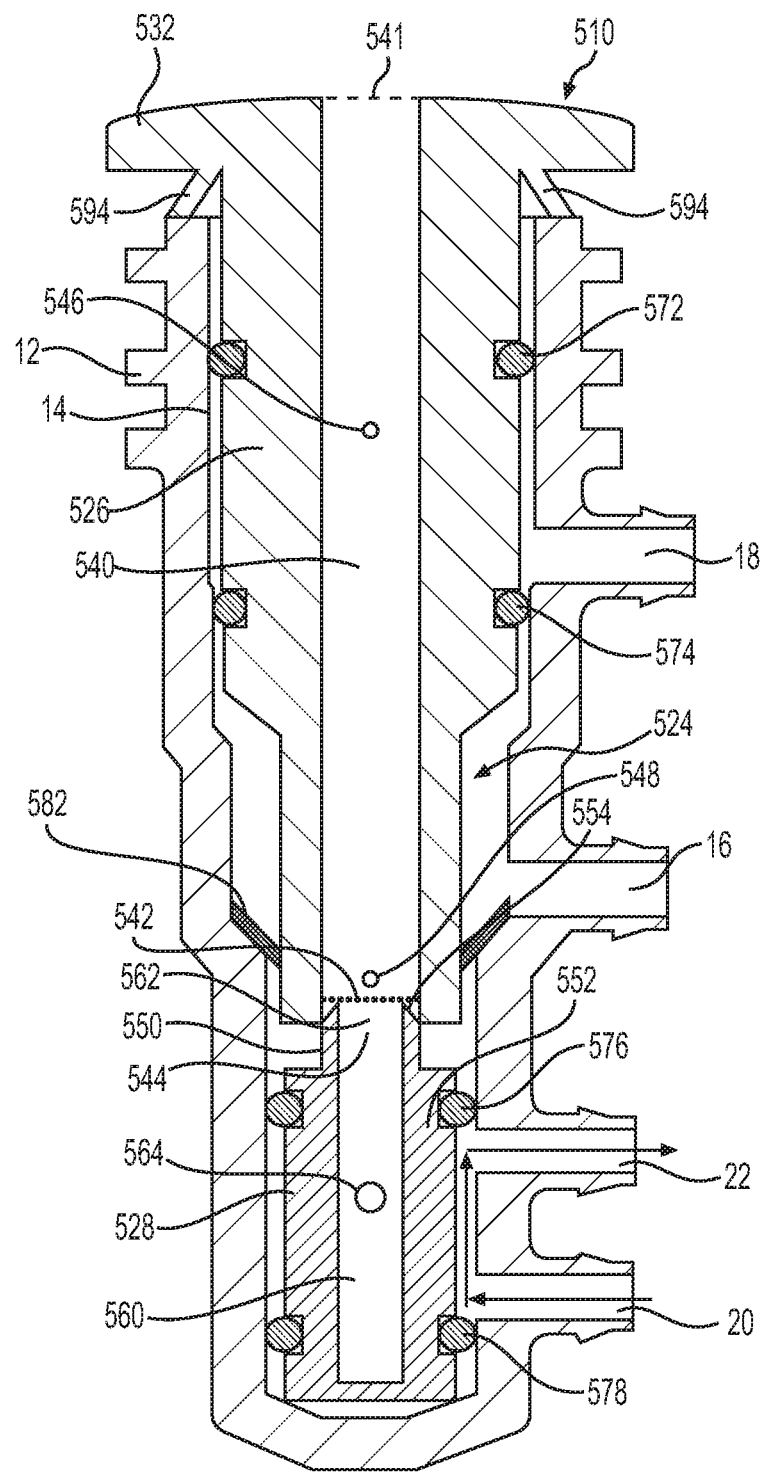
Figure 5C:
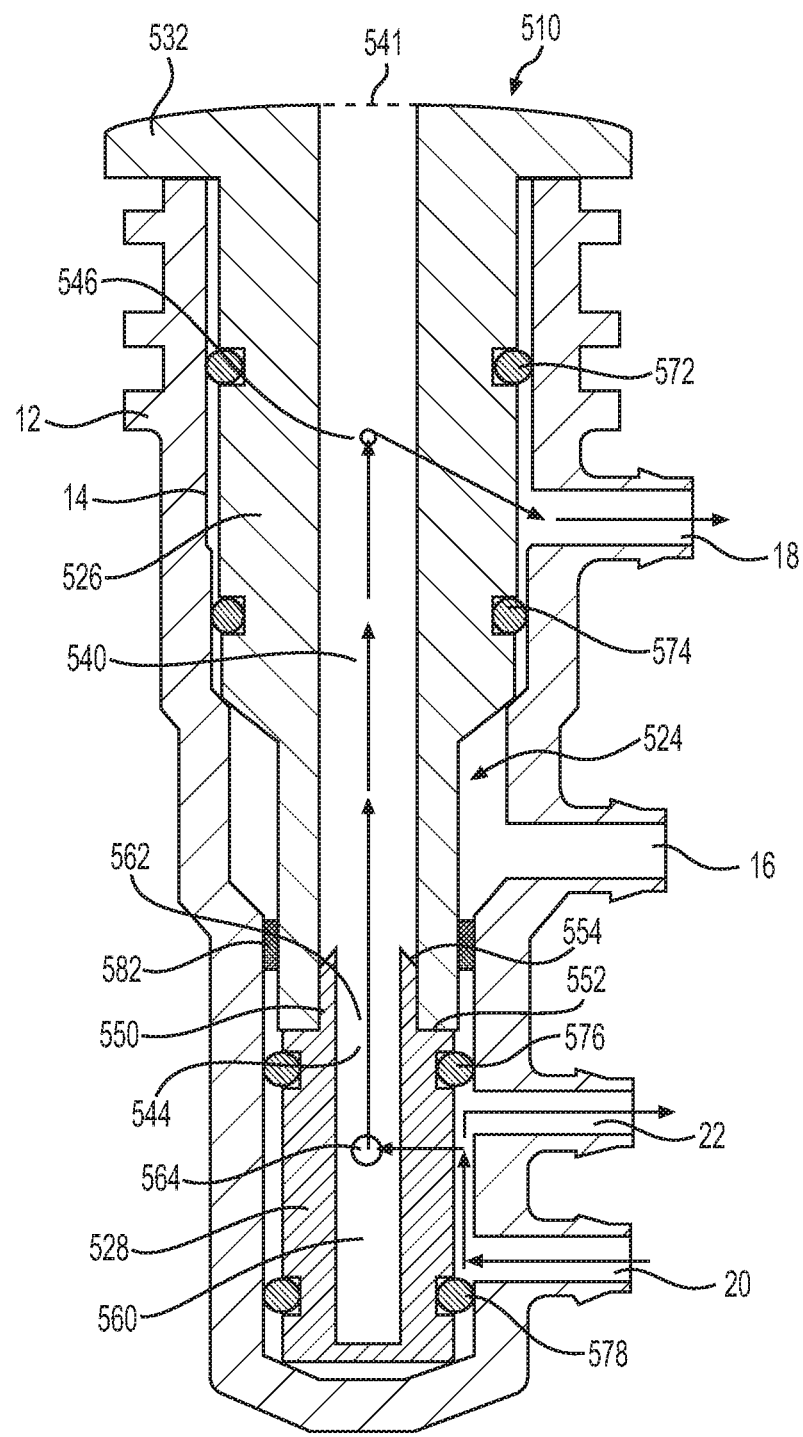

FIGS. 5A-5C show a cross-sectional view of an exemplary valve 500 in valve cylinder 12. Valve 500 may have a valve stem 524. Valve stem 524 may have a proximal member 526 and a distal member 528. Portions of valve stem 524 including proximal member 526 and distal member 528, may be made from metal (e.g., stainless steel, titanium, aluminum, etc.), from a polymer (e.g. polycarbonate, ABS, HDPE, Nylon, PEEK, thermoplastic, plastic, etc.), or from any other suitable material. Proximal member 526 and distal member 528 may be made from the same material or from different materials. Proximal member 526 and/or distal member 528 may be formed from a single, continuous material.

Proximal member 526 may include a button 532. Button 532 may be formed as one continuous structure with the rest of proximal member 526, or button 532 may be a separate structure attached to the rest of proximal member 526. Button 532 may have an outer circumference that is wider than a proximal opening of valve cylinder 12, so that when button 532 is depressed, button 532 cannot pass through the proximal opening of valve cylinder 12.

Proximal member 526 may have a proximal lumen 540. Proximal member 526 may have a generally annular shape around lumen 540. Proximal lumen 540 may have a proximalmost opening 541 on a proximalmost end of proximal member 526. For example, proximal lumen 540 may be open on a proximalmost side of button 532. Proximal opening 541 is shown with dashes to indicate that, as discussed below, proximal opening 541 may be covered by an operator (e.g., by the finger or thumb of an operator).

As shown in FIGS. 5A and 5B, a membrane 542 may extend completely across proximal lumen 540 toward a distal end 544 of proximal lumen 540. For example, membrane 542 may be a small distance from a distalmost end of proximal lumen 540. Alternatively, membrane 542 may be at a distalmost end of proximal lumen 540. Membrane 542 may be formed of a thin material. Aspects of membrane 542 will be discussed in further detail with reference to FIGS. 5B-5C.

A proximal aperture 546 may be formed in, and extend completely through, a wall of proximal member 526 and may fluidly connect proximal lumen 540 to an area external to proximal member 526. Although one proximal aperture 546 is shown in FIGS. 5A-5C, any number of proximal apertures may be used. One or more air apertures 548 may also be formed in, and extend completely through, a wall of proximal member 526 and may fluidly connect proximal lumen 540 to an area external to proximal member 526. Although only one air aperture 548 is shown, any suitable number of apertures may be utilized.

Distal member 528 may include a neck 550 on a proximal end of distal member 528. Neck 550 may have an outer diameter that is smaller than a diameter of lumen 540. Neck 550 may terminate distally in a shoulder 552. Neck 550 may have a proximal tapered portion 554. A distal lumen 560 may pass through distal member 528, including neck 550. Distal lumen 560 may be open on a proximalmost side of distal member 528 (e.g., on a proximalmost end 562 of neck 550) and may be closed on a distalmost side of distal member 528. A diameter of distal lumen 560 may be smaller than a diameter of proximal lumen 540. Tapered portion 554 may taper from an initial outer diameter (at a proximal end) until its outer diameter is substantially the same as a diameter of distal lumen 560. The proximalmost end of tapered portion 554 may form a sufficiently sharp annular ring to cut through, puncture, or otherwise remove membrane 542 under sufficient force. Portions of membrane 542 that are severed by tapered portion 554 may be flushed away by fluids flowing through valve 510 (further details of the flushing process are discussed below) or may remain within valve 510. A distal aperture 564 may be formed in, and extend completely through, a wall of distal member 528 and may fluidly connect distal lumen 560 to an area external to distal member 528. Although one distal aperture 564 is shown in FIGS. 5A-5C, any number of distal apertures may be used.

Neck 550 may be slidably received within proximal lumen 540 so that distal lumen 60 is in fluid communication with proximal lumen 540. Proximal lumen 540 and/or neck 550 may have features (e.g., indentations, protrusions, tabs, etc.) (not shown) that retain neck 550 within lumen 540 and prevent a proximalmost end 562 of neck 550 from exiting a distalmost end 544 of proximal lumen 540.

Valve stem 530 may be fitted with one or more seals. For example, valve stem 530 may include, in a direction from proximal to distal, a first seal 572, a second seal 574, a third seal 576, and a fourth seal 578. Seals 572, 574, 576, and 578 may be, for example, O-rings. Seals 572, 574, 576, and 578 may be formed from an elastomeric material. Valve stem 530 may also include a one-way seal 582, which may be made of the same or different material as seals 572, 574, 576, and 578 (e.g., an elastomeric material). One-way seal 582 may permit passage of fluid or other substances proximally past one-way seal 582 but may not permit passage of fluid or other substances distally past one-way seal 582 due to its flexibility and arrangement relative to its contacted structure. First seal 572 and second seal 574 may be disposed on proximal member 526. Third seal 576 and fourth seal 578 may be disposed on distal member 528. One-way seal 582 may be disposed on proximal member 526 between second seal 574 and third seal 576. Alternatively, seals 572, 574, 576, 578 and one-way seal 582 may be disposed on alternative portions of valve stem 530 or in different orders. Proximal aperture 546 may be disposed between first seal 572 and second seal 574. Distal aperture 564 may be disposed between third seal 576 and fourth seal 578.

Seals 572, 574, 576, and 578 may be configured so as to form a slidable interference fit between seals 572, 574, 576, and 578 and surface 14. Thus, valve stem 530 can move relative to surface 14, but fluids (e.g. water and air) cannot move between seals 572, 574, 576, and 578 and surface 14. Thus, seals 572, 574, 576, and 578 prevent movement of fluids external to valve 10 in a proximal or distal direction past seals 572, 574, 576, and 578.

An inner diameter of one-way seal 582 may be sized so that there is a slight interference between an external surface of proximal member 526 and the inner diameter of one-way seal 582, so that a tight seal is formed. An outer diameter of one-way seal 582 may be sized so as to form a slight interference fit with a portion of surface 14. A thin flap of one-way seal 582 may extend radially outward from proximal member 526 at an angle transverse to a longitudinal axis of proximal member 526. For example, the thin flap may extend at an angle between 10 degrees and 80 degrees relative to a longitudinal axis of proximal member 526. The flap of one-way seal 582 may be expandable so that when fluid (e.g., water or air) moves in a distal direction toward one-way seal 582, a positive pressure will expand the flap, maintaining a seal between one-way seal 582 and surface 14. Fluid moving proximally toward one-way seal 582 will also create a positive pressure, but the positive pressure will produce a force normal to a longitudinal axis of proximal member 526 to radially compress the flap of one-way seal 582. Thus, fluid (e.g., air or water) is permitted to move proximally past one-way seal 582, between one-way seal 582 and surface 14. Whereas one-way seal 82 of valve 10 may be disposed distally of air aperture 48, one-way seal 582 of valve 510 may be disposed proximally of air aperture 548.

FIG. 5A shows valve 510 in a first configuration and/or a second configuration. In the first configuration of valve 510, neither air nor water is delivered to any outlets of valve 510 and will vent through proximalmost opening 541 to the atmosphere.

In the second configuration, air is delivered to an air channel of an endoscope but water is not delivered to any channel. The first configuration and second configuration may differ only in that proximalmost opening 541 at a proximalmost end of proximal lumen 540 is left open in the first configuration and is blocked (e.g., by an operator's thumb or finger) in the second configuration. In the first and second configurations, button 532 may not be pushed down. Valve 510 may include features such as tactile feedback features (not shown) to indicate that valve 510 is in a proper position within valve cylinder 12. For example, valve 510 can include ridges, bumps, or other protrusions on an outside surface of proximal member 526. Proximalmost end 562 of distal lumen 560 (and neck 550) may be distal of membrane 542 so that proximal lumen 540 is not in fluid communication with distal lumen 560.

In the first and second configurations, water inlet 20 may be distal to fourth seal 578. Water outlet 22 may be between third seal 576 and fourth seal 578. Thus, water from water inlet 20 may not move proximally of fourth seal 578. Water outlet 22 is surrounded by third seal 576 and fourth seal 578, and therefore fluids (air and water) cannot move longitudinally to water outlet 22 along surfaces 14 of cylinder 12. And because membrane 542 is in place, distal lumen 560 and proximal lumen 540 are not in fluid communication. Thus, no fluids may exit water outlet 22.

In the first configuration (e.g., when proximalmost opening 541 is not covered and neither air nor water is delivered), as shown in dashed-line arrows on FIG. 5A, air may enter from air inlet 16 and then pass around a circumference of proximal member 526 of valve stem 524 to air aperture 548. Air will enter air aperture 548 instead of passing out air outlet 18 because proximalmost opening 541 venting to the atmosphere provides the path of least resistance. Air may then vent proximally out of proximalmost opening 541. Any air that would exit aperture 546 would be trapped between first seal 572 and second seal 574, so air will instead vent from proximalmost opening 541. Air may not travel distally past third seal 576 and thus may not exit water outlet 522. Air inlet 516 may be proximal of third seal 576 but distal to one-way seal 582. Air entering from air inlet 16 will not travel proximally past one-way seal 582 toward air outlet 18, because the path of least resistance will be for air to vent from proximalmost opening 541, and therefore air will not exit air outlet 18. Thus, in the first configuration, neither air nor water is delivered.

In the second configuration, also shown in FIG. 5A, proximalmost opening 541 may be covered by, for example, an operator's thumb or finger. Proximalmost opening 541 may also be covered in the third and fourth configurations, discussed below. Otherwise, the second configuration may be identical to the first configuration, e.g., all of the structures of valve 510 are in the same locations relative to one another and cylinder 12. Because air can no longer vent out of proximalmost opening 541, as shown in solid-line arrows on FIG. 1A, air entering from air inlet 16 may travel proximally past one-way seal 582. Thus, air entering from air inlet 16 may pass through air outlet 18 to deliver air to an air channel of an endoscope. Air from air inlet 16 may not pass proximally of second seal 574 and thus may not enter proximal aperture 546. Air entering aperture 548 cannot exit proximalmost opening 541 as it is covered. Thus, in the second configuration, valve 510 will deliver air to an air channel of the endoscope.

FIG. 5B shows valve 510 in a third configuration, in which water is delivered to a water channel of the endoscope but air is not delivered to any endoscope channel. To transition from the second configuration to the third configuration, button 532 may be depressed part-way. For example, button 532 may be depressed until a pliable feature on a distal surface of button 532 is in contact with an outer, proximal surface of cylinder 12. For example, tabs 594 may contact an outer surface of cylinder 12. Contact of features such as tabs 594 may cause tactile feedback to an operator to indicate that valve 10 is in the third configuration. Tabs 594 are merely exemplary, and any suitable feature may be used. For example, an annular flap/flange, expanded inflatable features, frangible piece, or other feature may be used. Tabs 594 may be made of the same material as button 532 or from a different material.

In transitioning from the second configuration to the third configuration, both proximal member 526 and distal member 528 may translate distally relative to cylinder 512, as a result of button 532 being pressed downward. Membrane 542 may be sufficiently resilient that a force on button 532 to transition valve 510 from the second configuration to the third configuration may not cause a proximalmost end of neck 550 to break through membrane 542. Therefore, membrane 542 may remain intact in the third configuration, and a force on neck 550 from membrane 542 may cause a distal translation of distal member 528 along with proximal member 526. Distal member 528 (and proximal member 526) may translate distally until distal member 528 rests on a distal surface of cylinder 12, or until tabs 594 contact an upper, proximal surface of cylinder 12. Additionally or alternatively, a frictional force between an outer surface of neck 550 and an inner surface of proximal lumen 540 may cause distal member 528 to move in unison with proximal member 526.

In the third configuration, fourth seal 578 may be distal to water inlet 20. Third seal 576 may be proximal of water outlet 22. Thus, as shown in solid-line arrows, water from water inlet 20 may not move distally past fourth seal 578 but may move through water outlet 22 and through a water channel of an endoscope. Although water may move through distal aperture 564, water may not move proximally past membrane 542, which may be resilient enough to block proximal movement of water. Thus, water may not enter proximal lumen 540. Water also may not move proximally past third seal 576. One-way seal 582 may be distal to air inlet 16 so air can not pass to enter air aperture 548. Second seal 574 may be proximal of air inlet 16. Thus, air from air inlet 16 may not move into proximal lumen 540 through air aperture 548 or past seal 574, thus will not exit air outlet 18. As a result, in the third configuration, the only fluid flow to the endoscope sheath is that of water through the water channel.

Valve 510 may be transitioned from the third configuration back to the first/second configuration. For example, valve 510 may have a spring (not shown) or other feature which biases valve 510 to the first configuration. Alternatively, valve 510 may be transitioned from the third configuration (or the first/second configuration) to the fourth configuration.

As shown in FIG. 5C, the fourth configuration facilitates flushing of water from water inlet 20 through both water outlet 22 and air outlet 18. The fourth configuration may be referred to as the cleaning configuration of valve 510. To move from the third configuration to the fourth configuration, button 532 may be depressed until tabs 594 are collapsed against a surface of cylinder 12. Substantially more force may be required to transition valve 150 to the fourth configuration than to the third configuration. While button 532 is depressed part-way in the third configuration, button 532 may be fully depressed in the fourth configuration. In the fourth configuration, tabs 594 may break (e.g., by cracking off at a proximal end of tabs 594) or bend flat so as to be parallel with a proximal surface of button 532 and/or a proximal surface of endoscope cylinder 12. A certain, minimum amount of force may be required to bend or break tabs 94.

Because distal member 528 already rested on a distal surface of cylinder 12 in the third configuration, distal member 528 may not translate distally along with proximal member 526 when button 532 is depressed fully. Translation of proximal member 526 distally relative to distal member 528 may cause proximal tapered portion 554 to pierce membrane 542 and thereby fluidly connect distal lumen 560 and proximal lumen 540. In the fourth configuration, proximal tapered portion 554 of distal member 528 may be proximal of the original location of membrane 542. Therefore, as shown with solid-line arrows, in the fourth configuration of valve 510, water may travel from water inlet 20 and out of water outlet 22, as in the third configuration of valve 510. However, unlike the third configuration, the fourth configuration also permits water to travel into proximal aperture 564, through distal lumen 560, into proximal lumen 540, and out of proximal aperture 546, so that water may flow between valve stem 530 and a surface of valve cylinder 12 to air outlet 18. Because air aperture 548 may be covered by neck portion 550 in the fourth configuration, water may not pass through air aperture 548.

The fourth configuration should not be used while an endoscope is inside of a body lumen of a patient. Valve 510 may contain mechanisms to prevent an operator from unintentionally transitioning valve 510 to the fourth configuration. For example, tabs 594 may provide resistance or other tactile feedback against pushing down button 532 past the third configuration. An operator may also receive tactile feedback from a distal end of distal member 528 contacting a distal surface of valve cylinder 12 in the third configuration, indicating to the operator that button 532 should not be further depressed while an endoscope is in use during a patient procedure. Additionally or alternatively, other methods may be used to prevent accidental transition of valve 510 into the fourth configuration. For example, a deformable mechanical stop may provide audible feedback (e.g., a "click" sound), valve 510 could require rotation prior to transitioning to the fourth configuration, and/or a visual indicator may provide feedback to an operator.

Because membrane 542 is broken in the fourth configuration, valve 510 may not again be used in any of the first, second, or third configurations. Therefore, valve 510 is a single-use valve, for use during only one pre-processing cleaning step. Alternatively, after use in one pre-processing cleaning, valve 510 could be used as only a pre-processing cleaning valve 510 without use during patient procedures. Alternatively, membrane 542 may be a strong, reusable seal that could be reset following use so that valve 510 is reusable over multiple procedures.

In order to make use of valve 510, an operator may insert valve 510 into valve cylinder 12 of an endoscope prior to a procedure. During the procedure, the operator may use valve 510 in the first, second, and/or third configurations, depending on the operator's desire to make use of air or water during the procedure. Following the procedure, the endoscope may be removed from the patient for reprocessing. Button 532 may be fully depressed so that valve 510 transitions to the fourth configuration. Valve 510 may flush water through the air and water channels for a predetermined amount of time (e.g., thirty seconds). After flushing is complete, an operator could either move button 532 proximally to disable the flow of water or could simply remove valve 510 from valve cylinder 12. Alternatively, button 532 may automatically move proximally to disable the flow of water. The endoscope would be subject to further reprocessing, and valve 510 may be disposed.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A valve for use in an endoscope, the valve comprising:
   a proximal valve stem member having a first lumen extending from a proximal opening at a proximalmost end of the proximal valve stem member to a distal opening at a distalmost end of the proximal valve stem member, wherein a membrane within the first lumen forms a fluid-tight barrier between the proximal opening and the distal opening; and
   a distal valve stem member having a second lumen with a proximal opening at a proximalmost end of the distal valve stem member;
   wherein the proximalmost end of distal valve stem member is received within the distal opening of the first lumen, and wherein the distal valve stem is movable relative to the proximal valve stem member;
   wherein the valve has a first configuration for delivering air to an air channel of the endoscope, a second configuration for delivering water to a water channel of the endoscope, and a third configuration for delivering water to the air channel of the endoscope, and wherein, in the first and second configurations, the proximalmost end of the distal valve stem member is distal to an original location of the membrane, and, wherein transitioning from the second configuration to the third configuration includes puncturing the membrane and moving the proximalmost end of the distal valve stem to a position proximal to the original location of the membrane.

2. The valve of claim 1, wherein the distal valve stem member has a shoulder that is contacted by the distalmost end of the proximal valve stem member in the third configuration.

3. The valve of claim 1, wherein the proximal valve stem member includes a first aperture formed through a wall of the proximal valve stem member, and wherein the first aperture is in fluid communication with the first lumen.

4. The valve of claim 3, wherein the proximal valve stem member includes a second aperture formed through the wall of the proximal valve stem member, and wherein the second aperture is in fluid communication with the first lumen.

5. The valve of claim 1, wherein the second lumen is closed at a distalmost end of the second lumen.

6. The valve of claim 5, wherein the distal valve stem member has a third aperture formed through a wall of the distal valve stem member, and wherein the third aperture is in fluid communication with the second lumen.

7. The valve of claim 1, wherein the proximal valve stem member includes a button configured to be contacted by a finger of an operator.

8. The valve of claim 7, wherein a proximal surface of the button is at the proximalmost end of the proximal valve stem member.

9. The valve of claim 7, wherein the proximal valve stem member includes at least one tab on a distal surface of the button.

10. The valve of claim 1, wherein at least one seal is disposed on an external surface of the distal valve stem member.

11. The valve of claim 1, wherein at least one O-ring seal is disposed on an external surface of the proximal valve stem member.

12. The valve of claim 1, wherein a one-way seal is disposed on an external surface of the proximal valve stem member.

13. A valve for use in an endoscope, the valve comprising:
   a proximal valve stem member having a first lumen extending from a proximal opening at a proximalmost end of the proximal valve stem member to a distal opening at a distalmost end of the proximal valve stem member, wherein a membrane within the first lumen forms a fluid-tight barrier between the proximal opening and the distal opening; and
   a distal valve stem member received within the distal opening of the first lumen;
   wherein, in a first configuration of the valve, the valve is capable of delivering air to an air channel of the endoscope, in a second configuration of the valve, the valve is capable of delivering water to a water channel of the endoscope, and, in a third configuration of the valve, the valve is capable of delivering water to the air channel of the endoscope, wherein, in the first and second configurations, the proximalmost end of the distal valve stem member is distal to an original location of the membrane, and, in the third configuration, the membrane is punctured and the proximalmost end of the distal valve stem is proximal to the original location of the membrane.

14. The valve of claim 13, wherein the distal valve stem member has a second lumen with a proximal opening at a proximalmost end of the distal valve stem member, wherein, in the first configuration, the first lumen and the second lumen are not in fluid communication, and wherein, in the second configuration, the first lumen and the second lumen are in fluid communication.

15. The valve of claim 14, wherein the second lumen is closed at a distalmost end of the second lumen, wherein the distal valve stem member has an aperture formed through a wall of the distal valve stem member, and wherein the aperture is in fluid communication with the second lumen.

16. The valve of claim 13, wherein the proximal valve stem member includes first and second apertures through a wall of the proximal valve stem member, and wherein each of the first and second aperture is in fluid communication with the first lumen.

17. A method of delivering air and water, the method comprising:
   via a valve in a first configuration, delivering air to an air channel of a medical device;
   transitioning the valve from the first configuration to a second configuration to deliver water to a water channel of the medical device; and
   transitioning the valve from the second configuration to a third configuration to deliver the water to the air channel of the medical device,
   wherein the valve includes:
      a proximal valve stem member having a first lumen extending from a proximal opening at a proximalmost end of the proximal valve stem member to a distal opening at a distalmost end of the proximal valve stem member, wherein a membrane within the first lumen forms a fluid-tight barrier between the proximal opening and the distal opening; and
      a distal valve stem member received within the distal opening of the first lumen;

wherein, in the first and second configurations, the proximalmost end of the distal valve stem member is distal to an original location of the membrane, and, wherein transitioning from the second configuration to the third configuration includes puncturing the membrane and moving the proximalmost end of the distal valve stem to a position proximal to the original location of the membrane.

18. The method of claim 17, further comprising transitioning the valve to the first configuration by covering a proximal hole of the valve; and wherein transitioning the valve to the second configuration includes depressing the valve part-way; and transitioning the valve to a third configuration includes fully depressing the valve.

19. The valve of claim 13, wherein, in the first configuration, a proximal hole of the valve is covered, in the second configuration the valve is depressed part-way, and in the third configuration, the valve is fully depressed.

20. The valve of claim 13, wherein the proximal valve stem member includes a button configured to be contacted by a finger of an operator.

\* \* \* \* \*